United States Patent
McDuff et al.

(10) Patent No.: US 10,799,182 B2
(45) Date of Patent: Oct. 13, 2020

(54) VIDEO-BASED PHYSIOLOGICAL MEASUREMENT USING NEURAL NETWORKS

(71) Applicant: Microsoft Technology Licensing, LLC, Redmond, WA (US)

(72) Inventors: Daniel Jonathan McDuff, Seattle, WA (US); Weixuan Chen, Cambridge, MA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 78 days.

(21) Appl. No.: 16/165,201

(22) Filed: Oct. 19, 2018

(65) Prior Publication Data

US 2020/0121256 A1   Apr. 23, 2020

(51) Int. Cl.
  *G06K 9/00*    (2006.01)
  *A61B 5/00*    (2006.01)
  (Continued)

(52) U.S. Cl.
  CPC .......... *A61B 5/7267* (2013.01); *A61B 5/0077* (2013.01); *A61B 5/02416* (2013.01);
  (Continued)

(58) Field of Classification Search
  None
  See application file for complete search history.

(56) References Cited

U.S. PATENT DOCUMENTS 9,402,546 B2   8/2016   Segman
9,730,643 B2   8/2017   Georgescu et al.
(Continued)

FOREIGN PATENT DOCUMENTS

CN   107180247 A   9/2017

OTHER PUBLICATIONS

Aarts, et al., "Non-contact heart rate monitoring utilizing camera photoplethysmography in the neonatal intensive care unit—A pilot study", In Journal of Early Human Development, vol. 89, Issue 12, Dec. 2013, pp. 943-948.
(Continued)

*Primary Examiner* — Atiba O Fitzpatrick

(57) ABSTRACT

Frames of a video frame sequence capturing one or more skin regions of a body are provided to a first neural network. The first neural network generates respective appearance representations based on the frames. An appearance representation generated based on a particular frame is indicative of a spatial distribution of a physiological signal across the particular frame. Simultaneously with providing the frames to the first neural network, the frames are also provided to a second neural network. The second neural network determines the physiological signal based on the frames. Determining the physiological signal by the second neural network includes applying the appearance representations, generated by the first neural network, to outputs of one or more layers of the second neural network to emphasize regions, in the frames, that exhibit relatively stronger presence of the physiological signal and deemphasize regions, in the frames, that exhibit relatively weaker presence of physiological signal.

20 Claims, 5 Drawing Sheets

(51) Int. Cl.
  G06T 7/00       (2017.01)
  G06N 3/08       (2006.01)
  G16H 30/20      (2018.01)
  A61B 5/024      (2006.01)
  A61B 5/08       (2006.01)
(52) U.S. Cl.
  CPC ............ *A61B 5/0816* (2013.01); *G06N 3/08* (2013.01); *G06T 7/0012* (2013.01); *G16H 30/20* (2018.01); *G06T 2207/10016* (2013.01); *G06T 2207/20081* (2013.01); *G06T 2207/20084* (2013.01); *G06T 2207/30088* (2013.01)

(56) References Cited

U.S. PATENT DOCUMENTS

| | | |
|---|---|---|
| 2011/0251493 A1 | 10/2011 | Poh et al. |
| 2017/0124432 A1 | 5/2017 | Chen et al. |
| 2017/0367590 A1 | 12/2017 | Sebe et al. |
| 2019/0139221 A1* | 5/2019 | Castro-Gonzalez .......................... A61B 5/1455 |

OTHER PUBLICATIONS

Bahdanau, et al., "Neural machine translation by jointly learning to align and translate", In Journal of Computing Research Repository, Sep. 2014, pp. 1-15.
Balakrishnan, et al., "Detecting pulse from head motions in video", In Proceedings of IEEE Conference on Computer Vision and Pattern Recognition, Jun. 23, 2013, pp. 3430-3437.
Ballas, et al., "Delving Deeper into Convolutional Networks for Learning Video Representations", In Proceedings of International Conference on Learning Representations, May 2, 2016, pp. 1-11.
Chaichulee, et al., "Multi-task convolutional neural network for patient detection and skin segmentation in continuous non-contact vital sign monitoring", In Proceedings of 12th IEEE International Conference on Automatic Face & Gesture Recognition, May 30, 2017, 7 Pages.
Donahue, et al., "Long-term recurrent convolutional networks for visual recognition and description", In Proceedings of the IEEE Computer Society Conference on Computer Vision and Pattern Recognition, vol. 39, Issue 4, Jun. 7, 2015, pp. 2625-2634.
Dosovitskiy, et al., "Flownet: Learning optical flow with convolutional networks", In Proceedings of the IEEE International Conference on Computer Vision, Dec. 7, 2015, pp. 2758-2766.
Estepp, et al., "Recovering Pulse Rate during Motion Artifact with a Multi-Imager Array for Non-Contact Imaging Photoplethysmography", In Proceedings of IEEE International Conference on Systems, Man and Cybernetics, Oct. 5, 2014, pp. 1462-1469.
Finn, et al., "Unsupervised Learning for Physical Interaction through Video Prediction", In Proceedings of Advances in Neural Information Processing Systems, Dec. 5, 2016, 9 Pages.
Haan, et al., "Improved motion robustness of remote-PPG by using the blood volume pulse signature", In Journal of Physiological Measurement, vol. 35, Aug. 27, 2014, pp. 1913-1926.
Haan, et al., "Robust pulse rate from chrominance-based rPPG", In Journal of IEEE Transactions on Biomedical Engineering, vol. 60, Issue 10, Oct. 2013, pp. 1-9.
Hurter, et al., "Cardiolens: remote physiological monitoring in a mixed reality environment", In Proceedings of 44th Conference on Computer Graphics and Interactive Techniques, Jul. 2017, 3 Pages.
Ilg, et al., "FlowNet 2.0: Evolution of Optical Flow Estimation with Deep Networks", In Proceedings of IEEE Conference on Computer Vision and Pattern Recognition, Jul. 21, 2017, pp. 1-9.
Lam, et al., "Robust heart rate measurement from video using select random patches", In Proceedings of IEEE International Conference on Computer Vision, Dec. 7, 2015, pp. 3640-3648.

Li, et al., "Remote heart rate measurement from face videos under realistic situations", In Proceedings of the IEEE conference on computer vision and pattern recognition, Jun. 23, 2014, pp. 4321-4328.
Li, et al., "VideoLSTM convolves, attends and flows for action recognition", In Journal of Computer Vision and Image Understanding, vol. 166, Jan. 2018, pp. 41-50.
McDuff, et al., "A survey of remote optical photoplethysmographic imaging methods", In Proceedings of 37th Annual International Conference of the IEEE Engineering in Medicine and Biology Society, Aug. 25, 2015, pp. 6398-6404.
McDuff, et al., "Improvements in remote cardio-pulmonary measurement using a five band digital camera", In Journal of IEEE Transactions on Biomedical Engineering, vol. 61, Issue 10, Oct. 2014, pp. 1-8.
Monkaresi, et al., "A machine learning approach to improve contactless heart rate monitoring using a webcam", In IEEE Journal of Biomedical and Health Informatics, vol. 18, Issue 4, Jul. 2014, pp. 1153-1160.
Ng, et al., "Beyond short snippets: Deep networks for video classification", In Proceedings of the IEEE Computer Society Conference on Computer Vision and Pattern Recognition, Jun. 7, 2015, pp. 1-9.
Osman, et al., "Supervised learning approach to remote heart rate estimation from facial videos", In Proceedings of 11th IEEE International Conference and Workshops on Automatic Face and Gesture Recognition, May 4, 2015, 6 Pages.
Poh, et al., "Advancements in noncontact, multiparameter physiological measurements using a webcam", In Journal of IEEE Transactions on Biomedical Engineering, vol. 58, Issue 1, Jan. 2011, pp. 7-11.
Poh, et al., "Non-contact, automated cardiac pulse measurements using video imaging and blind source separation", In Journal of Optics Express, vol. 18, Issue 10, May 7, 2010, pp. 10762-10774.
Rajpurkar, et al., "Cardiologist-Level Arrhythmia Detection with Convolutional Neural Networks", In Journal of Computing Research Repository, Jul. 2017, 9 Pages.
Shao, et al., "Noncontact Monitoring Breathing Pattern, Exhalation Flow Rate and Pulse Transit Time", In Journal of IEEE Transactions on Biomedical Engineering, vol. 61, Issue 11, Nov. 2014, pp. 1-8.
Sharma, et al., "Action recognition using visual attention", In Journal of Computing Research Repository, Nov. 2015, pp. 1-11.
Simonyan, et al., "Two-Stream Convolutional Networks for Action Recognition in Videos", In Proceedings of the 27th International Conference on Neural Information Processing Systems, vol. 1, Dec. 8, 2014, pp. 1-9.
Srivastava, et al., "Dropout: A Simple Way to Prevent Neural Networks from Overfitting", In Journal of Machine Learning Research, vol. 15, Issue 1, Jan. 2014, pp. 1929-1958.
Takano, et al., "Heart rate measurement based on a time-lapse image", In Journal of Medical Engineering & Physics, vol. 29, Issue 8, Oct. 2007.
Tarassenko, et al., "Non-contact video-based vital sign monitoring using ambient light and auto-regressive models", In Journal of Physiological Measurement, vol. 35, No. 5, Mar. 28, 2014, pp. 807-831.
Tran, et al., "Learning Spatiotemporal Features with 3D Convolutional Networks", In Proceedings of IEEE Conference on Computer Vision and Pattern Recognition, Jun. 24, 2014, pp. 1-16.
Tran, et al., "Two-stream flow-guided convolutional attention networks for action recognition", In Journal of Computing Research Repository, Aug. 2017, 10 Pages.
Tulyakov, et al., "Self-adaptive matrix completion for heart rate estimation from face videos under realistic conditions", In Proceedings of IEEE Conference on Computer Vision and Pattern Recognition, Jun. 27, 2016, pp. 2396-2404.
Verkruysse, et al., "Remote Plethysmographic Imaging Using Ambient Light", In Journal of Optics express, vol. 16, No. 26, Dec. 22, 2008, pp. 1-16.
Viola, et al., "Rapid object detection using a boosted cascade of simple features", In Proceedings of IEEE Computer Society Conference on Computer Vision and Pattern Recognition, Dec. 8, 2001, pp. 1-9.

(56) References Cited

OTHER PUBLICATIONS

Wang, et al., "A novel algorithm for remote photoplethysmography: spatial subspace rotation", In Journal of IEEE Transactions on Biomedical Engineering, Mar. 2015, pp. 1-11.
Wang, et al., "Algorithmic Principles of Remote-PPG", In Journal of IEEE Transactions on Biomedical Engineering, Mar. 2016, pp. 1-12.
Wang, et al., "Exploiting spatial redundancy of image sensor for motion robust rPPG", In Journal of IEEE Transactions on Biomedical Engineering, vol. 62, Issue 2, Feb. 2015, pp. 415-425.
Wu, et al., "Eulerian video magnification for revealing subtle changes in the world", In Journal of ACM Transactions on Graphics, vol. 31, Issue 4, Jul. 2012, 8 Pages.
Xu, et al., "Robust efficient estimation of heart rate pulse from video", In Journal of Biomedical Optics Express, vol. 5, Issue 4, Apr. 2014, pp. 1124-1135.
Xu, et al., "Show, Attend and Tell: Neural Image Caption Generation with Visual Attention", In Proceedings of the 32nd International Conference on Machine Learning, Jul. 6, 2015, 10 Pages.
Xue, et al., "Visual Dynamics: Probabilistic Future Frame Synthesis via Cross Convolutional Networks", In Journal of Computing Research Repository, Jul. 2016, pp. 1-9.
Yao, et al., "Video description generation incorporating spatio-temporal features and a soft-attention mechanism", In Journal of Computing Research Repository, Feb. 2015, 16 Pages.
Zeiler, Matthew D., "Adadelta: an adaptive learning rate method", In Journal of Computing Research Repository, Dec. 2012, 6 Pages.

* cited by examiner

VIDEO-BASED PHYSIOLOGICAL MEASUREMENT USING NEURAL NETWORKS

FIELD OF THE DISCLOSURE

The present disclosure relates generally to physiological measurements and, more particularly, to video-based physiological measurements using neural networks.

BACKGROUND

Non-contact video-based physiological measurement systems have many applications in health care and human-computer interactions. Such systems may utilize imaging techniques, such as imaging photoplethymography (iPPG) techniques, imaging ballistocardiography (iBCG) techniques and the like, to recover physiological signals from frames of a video. As an example, an iPPG system may recover a blood volume pulse (BVP) from frames of a video, the BVP pulse being representative of the volumetric change in blood close to the surface of the video subject's skin over time. As another example, an iBCG system may generate a ballistocardiogram by detecting small motions in a video subject's body that may be caused by the mechanical flow of blood in the video subject's body. Such physiological signals may, in turn, be utilized to recover physiological parameters, such as heart rate or respiration rate of the subject in the video. Non-contact video-based physiological measurement techniques have may advantages over traditional methods that utilize contact sensors to perform such measurements. For example: long-term contact sensor application of sensors often irritates the subject's skin; contact sensors may become corrupted by muscle or sensor movements, particularly in situations of high levels of motion by the subject; contact sensors may be impractical for use in some applications, such as in tele-health systems.

Currently available non-contact video-based physiological measurement systems typically utilize complex, multi-stage image processing techniques that may involve, for example, face-tracking and registration, skin recognition, color space transformations, and signal decomposition. Such typical multi-stage techniques often require hand-tuning and are generally difficult to implement. Moreover, the currently available techniques often lack desired accuracy. For example, the currently available techniques may be highly susceptible to noise resulting from subject's motion, non-constant lighting and video camera artifacts.

SUMMARY

In an embodiment, a computer-implemented method for measuring physiological parameters includes receiving a video fame sequence capturing one or more skin regions of a body, providing frames of the video frame sequence to a first neural network, and generating, using the first neural network, respective appearance representations based on the frames of the video frame sequence, wherein an appearance representation generated based on a particular frame of the video frame sequence is indicative of a spatial distribution of a physiological signal across the particular frame of the video frame sequence. The method also includes simultaneously with providing the frames of the video frame sequence to the first neural network, providing the frames to a second neural network, and determining, using the second neural network, the physiological signal based on the frames of the video frame sequence, including applying the appearance representations, generated by the first neural network, to outputs of one or more layers of the second neural network to emphasize regions, in the frames, that exhibit relatively stronger presence of the physiological signal and deemphasize regions, in the frames, that exhibit relatively weaker presence of physiological signal.

In another embodiment, a system for measuring physiological parameters comprises a data storage device that stores instructions for measuring physiological parameters based on frames of a video, and a processor configured to execute the instructions to perform a method including: receiving a video fame sequence capturing one or more skin regions of a body; providing frames of the video frame sequence to a first neural network; generating, using the first neural network, respective appearance representations based on the frames of the video frame sequence, wherein an appearance representation generated based on a particular frame of the video frame sequence is indicative of a spatial distribution of a physiological signal across the particular frame of the video frame sequence; simultaneously with providing the frames of the video frame sequence to the first neural network, providing the frames to a second neural network; and determining, using the second neural network, the physiological signal based on the frames of the video frame sequence, including applying the appearance representations, generated by the first neural network, to outputs of one or more layers of the second neural network to emphasize regions, in the frames, that exhibit relatively stronger presence of the physiological signal and deemphasize regions, in the frames, that exhibit relatively weaker presence of physiological signal.

In yet another embodiment, a tangible computer readable medium, or media, storing machine readable instructions that, when executed by one or more processors, cause the one or more processors to: receive a video fame sequence capturing one or more skin regions of a body; provide frames of the video frame sequence to a first neural network; generate, using the first neural network, respective appearance representations based on the frames of the video frame sequence, wherein an appearance representation generated based on a particular frame of the video frame sequence is indicative of a spatial distribution of a physiological signal across the particular frame of the video frame sequence; simultaneously with providing the frames of the video frame sequence to the first neural network, provide the frames to a second neural network; and determine, using the second neural network, the physiological signal based on the frames of the video frame sequence, including applying the appearance representations, generated by the first neural network, to outputs of one or more layers of the second neural network to emphasize regions, in the frames, that exhibit relatively stronger presence of the physiological signal and deemphasize regions, in the frames, that exhibit relatively weaker presence of physiological signal.

DETAILED DESCRIPTION

In various embodiments described below, a video-based physiological measurement system derives physiological signals and/or obtains physiological parameters, such as a heart rate, a breathing rate, etc., from frames of a video. The video-based physiological measurement system may include a first module that generates, based on frames of a video frame sequence, appearance representations indicative of a spatial distribution of a physiological signal across the frames of the video frame sequence over time. The video-based physiological measurement system may also include a second module that may operate on the frames of the video frame sequence, simultaneously with the first module, to recover the physiological signal from the frames of the video frame sequence. In the process of recovering the physiological signal, the second module may utilize the appearance representations to emphasize regions, within the frames, that exhibit relatively stronger measures of the physiological signal (e.g., skin regions and/or particular areas within the skin regions with relatively higher presence of the physiological signal) and to deemphasize regions, within the frames, that exhibit relatively weaker measures of the physiological signal (e.g., non-skin regions and/or particular areas within the skin regions with relatively lower presence of the physiological signal). In an embodiment, the first module and the second module comprises a respective neural network, such as a respective convolutional neural network (CNN). The neural network of the second module may be trained to obtain a physiological signal from detecting subtle light color changes and/or motions in video frames, and the neural network of the first module may be trained to obtain spatial distribution of the physiological signal in the video frames thereby identifying regions that exhibit relatively stronger physiological signals in the video frame. The spatial distribution of the physiological signal obtained by the first neural network may be provided as an input to the second neural network thereby focusing attention of the second neural network on the regions that exhibit relatively stronger physiological signals in the video frames being processed by the second neural network. The first neural network and the second neural network may be trained simultaneously, end-to-end, using supervised training with labeled data. These and other techniques described herein result in a simple end-to-end neural network implementation for physiological signal recovery and accurate physiological parameter determination from frames of a video, even if the subject of the video is non-stationary, exhibits relatively large movement and/or is not under constant lighting conditions, in at least some embodiments.

Figure 1:
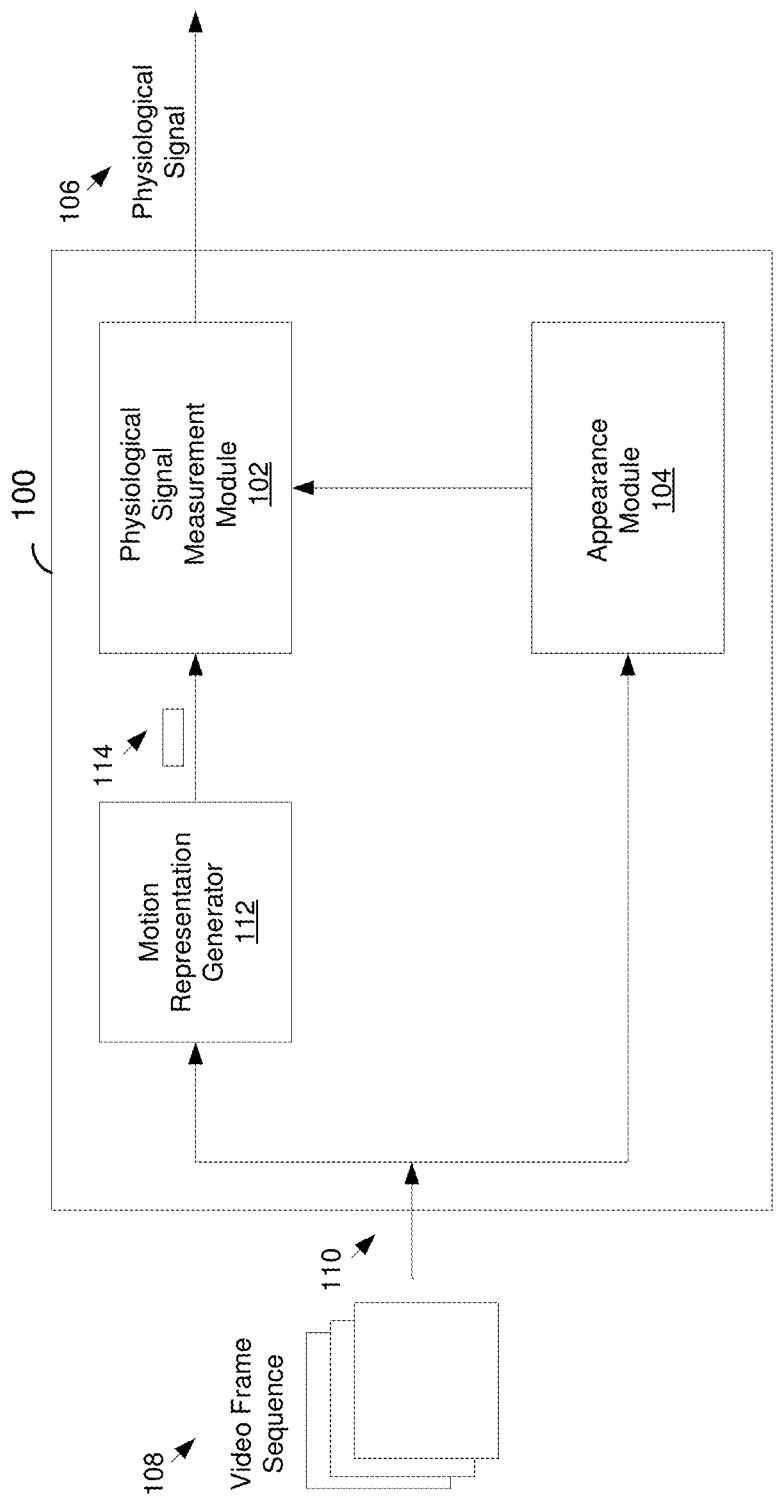
FIG. 1 is a block diagram of an example video-based physiological measurement system, according to an embodiment.

FIG. 1 is a block diagram of an example video-based physiological measurement system 100, according to an embodiment. The video-based physiological measurement system 100 includes a physiological signal measurement module 102 and an appearance module 104. Frames of a video frame sequence 108 may be provided to the physiological signal measurement module 102, and the physiological signal measurement module 102 may operate to recover a physiological signal 106 from the frames of the video frame sequences 108 provided to the physiological signal measurement module 102. The video frame sequence 108 may include frames of a video capturing a subject's face, for example, and/or other part of the subject's body. The video frame sequence 108 may be obtained from a remote camera, which may be a computer camera, a laptop camera, a smart phone camera, etc. The camera may be, for example, a multichannel camera (e.g., a red green blue (RGB) camera), a single channel camera (e.g., an infrared camera), or another suitable type of camera. The physiological signal 106 recovered by the physiological signal measurement module 102 may be a blood volume pulse (BVP) or a reparatory signal, for example. In other embodiments, other suitable physiological signals may be recovered. The physiological signal measurement module 102 may recover the physiological signal 106 by detecting changes in intensity (e.g., color) of light reflected from the subject's skin as captured by the video. The changes in light intensity reflected from the skin of the subject may be representative of the movement of blood in skin capillaries, or volumetric change in blood, with respect to time, close to the skin surface. Additionally, or alternatively, the physiological signal measurement module 102 may recover the physiological signal 106 by detecting subtle motions of the skin, that may be caused by the subject's breathing, as captured by the video.

In an embodiment, frames of the video frame sequence 108 may also be provided to the appearance module 104. The frames of the video frame sequence 108 may be provided to the appearance module 104 simultaneously (e.g., at the same time or in an overlapping manner) with being provided to the physiological signal measurement module 102. The appearance module 104 may operate on the frames simultaneously with the physiological signal measurement module 102 to detect spatial-temporal distribution of the physiological signal 106 in the frames of the video frame sequence 108. The appearance module 104 may detect regions within the frames that exhibit relatively stronger and relatively weaker measures of the physiological signal 106. For example, the appearance module 104 may assign weights corresponding to different regions (e.g., different pixels) within the frames, where relatively higher weights may be assigned to regions that exhibit stronger measures of the physiological signal being measured and lead to more accurate recovery of the physiological signal being measured, and relatively lower weights may be assigned to regions that exhibit weaker measures of physiological signal and lead to less accurate recovery of the physiological signal. The appearance representation (e.g., in the form of weights) may be provided to the physiological signal measurement module 102 and may be used by the physiological signal measurement module 102 during the process of recovering the physiological signal, to emphasize the regions that exhibit the stronger measures of the physiological signal and to deemphasize the regions that exhibit the weaker measures of physiological signal. Emphasizing the regions that exhibit stronger measures of physiological signal and deemphasizing the regions that exhibit the weaker measures of physiological signal may result in more accurate recovery of the physiological signal by the physiological signal measurement module 102 and may lead to a more accurate measure of the physiological parameter that may be determined based on the physiological signal, in at least some embodiments. The appearance representations may additionally be provided as a separate output of the video-based physiological measurement system 100, in an embodiment. For example, the appearance representations may be used to provide (e.g., display) the detected spatial-temporal distribution of the physiological signal 106 within the frames. The spatial-temporal distribution of the physiological signal 106 may serve as an additional tool in conjunction with the physiological signal 106 and/or physiological parameters obtained based on the physiological signal 106 to assess health of the subject, for example.

With continued reference to FIG. 1, the physiological measurement system 100 may include an input 110 for receiving the video frame sequence 108. The input 110 may be a multi-channel input. For example, the input 110 may comprise three channels, each channel corresponding to a respective RGB channel of a camera output. Accordingly, in an embodiment in which the video frame sequence 108 is obtained from an RGB camera, each respective channel output of the RGB camera may be provided to a corresponding channel in the input 110. In an embodiment in which the video frame sequence 108 is obtained from a single channel camera, such as an infrared camera, the frames in the video frame sequence 108 may be duplicated to generate three identical channel inputs, and the three identical channel inputs may be provided to respective channels in the inputs 110. In another embodiment, the input 110 may comprise a single channel, and the single channel camera output may be provided to the single channel of the input 110.

In an embodiment, the physiological signal measurement module 102 may operate on a motion representation 114 generated by a motion representation generator 112 based on a difference between consecutive two or more video frames in the video frame sequence 108, as will be described in more detail below. Accordingly, the physiological signal measurement module 102 may recover the physiological signal 106 from the motion representation 114 generated based on two or more consecutive video frames in the video frame sequence 108, in this embodiment. The appearance module 104, on the other hand, may operate on individual frames of the video frame sequence 108, and may detect the distribution of the physiological signal in each individual frame in the video frame sequence 108.

In an embodiment, each of the physiological signal measurement module 102 and the appearance module 104 comprises a neural network. For example, in an embodiment, the appearance module 104 comprises a first neural network and the physiological signal measurement module 102 comprises a second neural network. The first neural network is a convolutional attenuation neural network (CAN) trained to determine appearance representations, or attention masks, based on frames of the video sequence 108, in an embodiment. The second neural network is a convolutional neural network (CNN) trained to recover the physiological signal 106 from the frames of the video sequence 108, in an embodiment. The first neural network and the second neural network may be trained simultaneously using end-to-end supervised training, for example. As an example, in an embodiment in which the physiological signal 106 to be recovered is a blood volume pulse for determining a hear rate, simultaneous end-to-end training may be performed using (i) videos obtained from a plurality of subjects and (ii) corresponding test data obtained by measuring the blood volume pulse using a finger probe on each of the subjects. As another example, in an embodiment in which the physiological signal 106 to be recovered is a respiratory signal for determining a breathing rate, simultaneous end-to-end training of the first neural network and the second neural network may be performed using (i) videos obtained from a plurality of subjects and (ii) corresponding test data obtained by measuring the respiration signal using a chest belt on each of the subjects.

Generally, the physiological signal measurement module 102 may detect color changes and/or motion changes in frames of the video frame sequence 108 based on changes in reflection of light as seen by the camera generating the video frame sequence 108. In an embodiment, the color changes and/or motion changes may be modeled using dichromatic reflection model (DRM), for example. According to the DMR model, the light reflection value at the k-th pixel of an image can be written as $$C_k(t) = I(t) \cdot (v_s(t) + v_d(t)) + v_n(t) \qquad \text{Equation 1}$$

where $C_k(t)$ denotes the light reflection value at the pixel k, $I(t)$ is the luminance intensity level, $v_s(t)$ is a specular reflection component that modulates the luminance intensity level $I(t)$, $v_d(t)$ is a diffuse reflection component that modulates the luminance intensity level $I(t)$, and $v_n(t)$ is the quantization noise of the camera sensor in the camera. Depending on the type of camera used to obtain the video frame sequence, $C_k(t)$ may be a single light reflection value corresponding to the pixel k, or a vector of RGB values, for example. The luminance intensity level $I(t)$ may generally be dependent on the light source as well as the distance between the light source, the skin tissue being captured with the light source, and the camera. The specular reflection component $v_s(t)$, the diffuse reflection component $v_d(t)$ and the luminance intensity level $I(t)$ can each be decomposed into a stationary (i.e., time-independent) component and a time-dependent component. For example, the diffuse reflection component $v_d(t)$ in Equation 1 can be written, in a decomposed form, as $$v_d(t) = u_d \cdot d_0 + u_p \cdot p(t) \qquad \text{Equation 2}$$

where $u_d$ is the unit color vector of the skin-tissue in the image, $d_0$ is the stationary reflection strength value, $u_p$ is the relative pulsatile strength caused in the image by the hemoglobin and melanin absorption in blood capillaries near the surface of the skin captured by the camera, and $p(t)$ is the physiological signal being measured. The specular reflection component $v_s(t)$ in Equation 1 can be written, in a decomposed form, as $$v_s(t) = u_s \cdot (s_0 + \Phi(m(t), p(t))) \qquad \text{Equation 3}$$

where $u_s$ is the unit color vector of the light source spectrum, $s_0$ is the stationary specular reflection strength value, and $\Phi(m(t), p(t))$ is the time-dependent component of specular reflection, wherein $m(t)$ denotes non-physical variations, such as flickering of the light source, head rotations and facial expressions, for example. The luminance intensity level $I(t)$ in Equation 1 can be written, in decomposed form, as $$I(t) = I_0 \cdot (1 + \Psi(m(t), p(t))) \qquad \text{Equation 4}$$

where $I_0$ is the stationary component of the luminance intensity, and $I_0 \cdot \Psi(m(t), p(t))$ is the luminance intensity variation observed by the camera.

The stationary component of the specular reflection component $v_s(t)$ and the stationary component of the diffuse reflection component $v_d(t)$ can be combined into a single component representing the stationary skin reflection $$u_c \cdot c_0 = u_s \cdot s_0 + u_d \cdot d_0 \qquad \text{Equation 5}$$

where is the unit color vector of the skin reflection and $c_0$ is the skin reflection strength. Substituting Equations 2, 3, 4 and 5 into Equation 1, $C_k(t)$ can be written as $$c_k(t)=I_0 \cdot (1+\Psi(m(t),p(t)))(u_c \cdot c_0 + u_s \cdot \Phi(m(t),p(t))) + u_p \cdot p(t)) + v_n(t) \quad \text{Equation 6}$$

In some cases, for example when the subject of the video is stationary and is under constant lighting conditions, the term m(t) is small. In such cases, the term m(t) inside the functions $\Psi(m(t), p(t))$ and $\Psi(m(t), p(t))$ may be ignored, and a linear relationship between $C_k(t)$ and p(t) may be assumed. In other situations, for example when the subject of the video is not stationary and/or is under varying lighting conditions, the term m(t) is not small and assuming a linear relationship between $C_k(t)$ and p(t) may lead to inaccurate results. In an embodiment, the physiological signal measurement module 102 may be trained to capture a non-liner relationship between $C_k(t)$ and p(t) resulting from the $\Psi(m(t), p(t))$ and $\Phi(m(t), p(t))$ terms in Equation 6. Because the physiological signal measurement module 102 captures the non-linear relationship between $C_k(t)$ and p(t), the physiological signal measurement module 102 recovers a more accurate p(t) from the video frames as compared to systems that ignore p(t) inside the functions $\Psi(m(t), p(t))$ and $\Phi(m(t), p(t))$, in at least some embodiments. The more accurate p(t) recovered from the video frames, in turn, leads to more accurate physiological parameters (e.g., heat rate, breathing rate, etc.) obtained from the recovered physiological signal p(t), as compared to systems that ignore the term m(t) inside the functions $\Psi(m(t), p(t))$ and $\Phi(m(t), p(t))$, in at least some embodiments.

As discussed above, the physiological signal measurement module 102 may operate on the motion representation 114 generated based on frames of the video frame sequence 108 by the motion representation generator 112. The motion representation generator 112 may generate the motion representation 114 based on a calculated frame differences between consecutive frames of the video frame sequence 108. In an embodiment, generating the motion representation may include, prior to calculating a frame difference between frames of the video frame sequence 108, spatially averaging pixels in the frames to reduce or eliminate camera quantization errors in the frames. For example, referring to Equation 7, spatial averaging of pixels in a frame may reduce or eliminate the camera quantization error term v(t), in an embodiment. To spatially average pixels in a frame, the motion representation generator 112 may down-sample the video frame image to a suitable size. For example, the motion representation generator 112 may utilize bicubic interpolation, or utilize another suitable technique, to down-sample a respective frame to a size of L pixels by L pixels, where L is a suitable integer. In an embodiment, a value of L is selected to balance suppressing camera noise present in the frame with retaining spatial resolution in the frame. In an embodiment, L is equal to 36. In other embodiments, other suitable values of L are utilized. The reflection model of the down-sampled video frame image may be written as $$C_l(t) \approx u_c \cdot I_0 \cdot c_0 + u_c \cdot I_0 \cdot c_0 \cdot \Psi(m(t),p(t)) + u \cdot I \cdot \Psi(m(t),p(t)) + u \cdot I \cdot p(t) \quad \text{Equation 8}$$

where $l=1, \ldots, L^2$ corresponds to the new pixel index in the down-sampled frame.

The motion representation generator 112 may then calculate a first order derivative of both sides of the Equation 8 with respect to time according to $$C_l'(t) \approx u_c \cdot I_0 \cdot c_0 \cdot \left(\frac{\partial \Psi}{\partial m}m'(t) + \frac{\partial \Psi}{\partial p}p'(t)\right) + \\ u_s \cdot I_0 \cdot \left(\frac{\partial \Phi}{\partial m}m'(t) + \frac{\partial \Phi}{\partial p}p'(t)\right) + u_p \cdot I_0 \cdot p'(t) \quad \text{Equation 9}$$

The first order derivative may reduce dependency of $C_l(t)$ in Equation 8 on the stationary skin reflection color component $u_c \cdot I_0 \cdot c_0$ which may generally be caused by the light source and the subject's skin tone. Generally, in supervised learning, the stationary skin reflection color component $u_c \cdot I_0 \cdot c_0$ varies between different subjects and lighting conditions in the training data used for training the physiological signal measurement module 102. In at least some embodiments in which supervised learning is utilized to train the physiological signal measurement module 102, such variation in different subjects and lighting conditions in the labeled data may make it more difficult to train the physiological signal measurement module 102 to discriminate the variance of interest in the $C_l(t)$ which is caused by the physiological signal p(t), in at least some situations. In some situations, such variation in different subjects and lighting conditions in the training data may also depend the learning on the training data. Accordingly, reducing the dependency of $C_l(t)$ in Equation 8 on the stationary skin reflection color component $u_c \cdot I_0 \cdot c_0$ may lead to better training of the physiological signal measurement module 102, at least when supervised learning with labeled data is utilized.

The stationary luminance intensity level term $I_0$ in Equation 9 may be spatially heterogeneous due to different distances from the light source in different videos (e.g., different video frame sequences 108) and different frames within the video frame sequences 108 and/or uneven skin contours in different videos (e.g., different video frame sequences 108) and different frames within the video frame sequences 108. To remove the stationary luminance intensity level term $I_0$ from Equation 9, the motion representation generator 112 may normalize the derivative $C_l'(t)$ by dividing both sides of Equation 9 by the temporal mean $\overline{C_l'(t)}$. Thus normalized derivative $C_l'(t)$ may be written as $$\frac{C_l'(t)}{\overline{C_l(t)}} \approx \frac{\partial \Psi}{\partial m}m'(t) + \frac{\partial \Psi}{\partial p}p'(t) + \text{diag}^{-1}(u_c)u_p \cdot \frac{1}{c_0} \cdot p'(t) + \\ \text{diag}^{-1}(u_c)u_s \cdot \frac{1}{c_0} \cdot \left(\frac{\partial \Phi}{\partial m}m'(t) + \frac{\partial \Phi}{\partial p}p'(t)\right) \quad \text{Equation 10}$$

In some embodiments, the motion representation generator 112 may compute the temporal mean $\overline{C_l'(t)}$ in Equation 10 pixel-by-pixel over frames of the video frame sequences 108 within short periods of time, the short periods of time including respective subsets of only a few (e.g., only two, only three, etc.) frames of the video frame sequence 108. Computing the temporal mean $\overline{C_l'(t)}$ over frames of the video frame sequences 108 within short periods of time may minimize occlusion and may prevent propagation of errors, in an embodiment. For example, in an embodiment, the motion representation generator 112 may compute the temporal mean $\overline{C_l'(t)}$ over each pair of consecutive frames of the video frame sequence 108 according to $$D_l(t) = \frac{C_l'(t)}{\overline{C_l(t)}} \sim \frac{C_l(t+\Delta t) - C_l(t)}{C_l(t+\Delta t) + C_l(t)} \quad \text{Equation 11}$$

where $D_l(t)$ is the motion representation 114, in an embodiment. In some embodiments, the motion representation generator 112 may clip $D_l(t)$ to diminish outliers in the $D_l(t)$ which may result from a relatively large motion component m'(t) and/or occlusion caused by temporal mean normalization. The final motion representation 114 may then be the clipped $D_l(t)$, in an embodiment.

In an embodiment in which a derivative motion representation is utilized, the physiological signal measurement module 102 and the appearance module 104 may be simultaneously trained using a first derivative of a gold-standard physiological signal $p'(t)=p(t+\Delta t)-p(t)$ as the training label. In some embodiments, the motion representation $D_l(t)$ and the first derivative of a gold-standard physiological signal $p'(t)$ is each scaled to unit standard deviation over the training video frame sequence being utilized. Scaling the clipped frame difference $D_l(t)$ and the first derivative of a gold-standard physiological signal $p'(t)$ may lead to higher convergence speed of stochastic gradient descent during the training, in at least some embodiments. In an embodiment in which a derivative of a gold-standard physiological signal $p'(t)$ is used as the labeled data, ensemble learning may be performed so that a more accurate physiological parameter (e.g., heart rate or breathing rate) based on a recovered physiological signal (e.g., blood volume pulse or respiratory signal) may subsequently be determined. For example, the physiological signal measurement module 102 and the appearance module 104 may be trained for multiple additional epochs (e.g., 16 additional epochs) after convergence is detected. The resulting physiological signals generated at each of the additional epochs may then be processed to determine dominant frequencies and to thereby calculate the physiological parameter. Frequency errors corresponding to each epoch may be determined by comparing the calculated physiological parameter with a real measured physiological parameter. The models of the physiological signal measurement module 102 and the appearance module 104 corresponding to the epoch with the smallest frequency error may then be selected to be subsequently used as the trained physiological signal measurement module 102 and the appearance module 104, respectively, in an embodiment.

Figure 2:
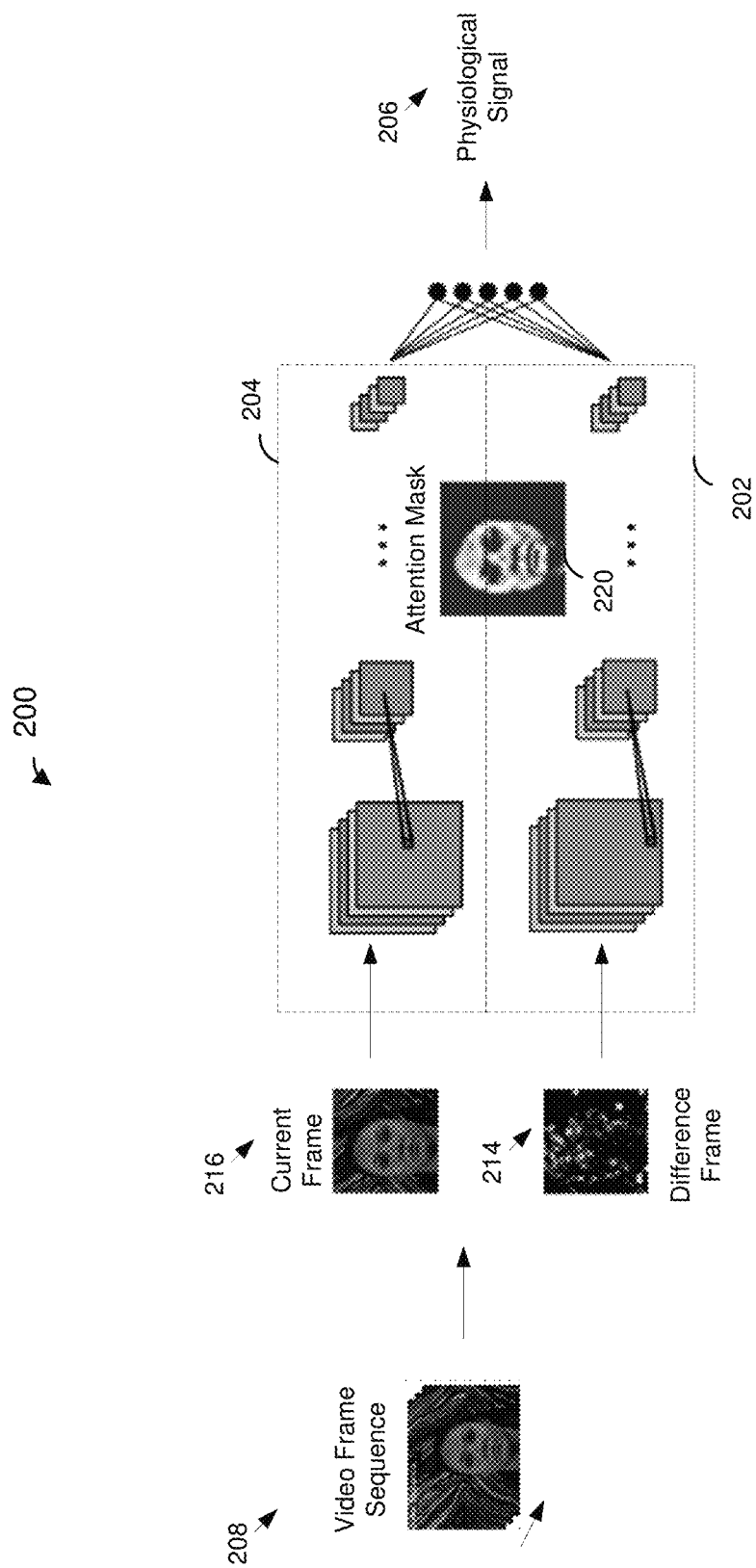
FIG. 2 is a block diagram illustrating operation of a video-based physiological measurement system such as the video-based physiological measurement system of FIG. 1, according to an embodiment.

Referring briefly to FIG. 2, operation of a video-based physiological measurement system 200, according to an embodiment, is illustrated. The video-based physiological measurement system 200 corresponds to the video-based physiological measurement system 100, according to an embodiment. In the embodiment of FIG. 2, a video frame sequence 208 of a human face is obtained. The video frame sequence 208 may be obtained from a remote camera, such as a laptop camera, a smart phone camera or the like. In other embodiments, the video frame sequence 208 may be obtained in other suitable manners. The video frame sequence 208 may be simultaneously provided to a physiological signal measurement module 202 and an appearance module 204. The physiological signal measurement module 202 corresponds to the physiological signal measurement module 102 of FIG. 1 and the appearance module 204 corresponds to the appearance module 104 of FIG. 1, in an embodiment.

With continued reference to FIG. 2, the physiological signal measurement module 202 may operate on a motion representation 214, generated based on frames of the video frame sequence 208, to recover a physiological signal p(t) from the motion representation 214. The motion representation 214 corresponds to the motion representation 114 generated by the motion representation generator 112 of FIG. 1, in an embodiment. In other embodiments, the motion representation 214 is generated in other suitable manners. The appearance module 204 may operate on each respective frame of the video frame sequence 208 to generate an attention mask 220. The attention mask 220 may be a representation, in each current frame 216, of distribution of the physiological signal p(t) being recovered by the physiological signal measurement module 202. The attention mask 220 may generally emphasize regions of the frame that exhibit relatively stronger measure of the physiological signal 206 and deemphasize regions of the current frame that exhibit relatively weaker measures of the physiological signal 206. The attention mask 220 may be provided to the physiological signal measurement module 202, and may be utilized in the process of recovering the physiological signal 206 by the physiological signal measurement module 202. For example, the attention mask 220 may be applied to adjust weights in the physiological signal measurement module 202, such as weights in one or more certain layers of a neural network of the physiological signal measurement module 202, so as to emphasize regions in the frames of the video frame sequence 208 that exhibit stronger measures of the physiological signal 206 and deemphasize regions that exhibit relatively weaker measures of the physiological signal 206.

Figure 3:
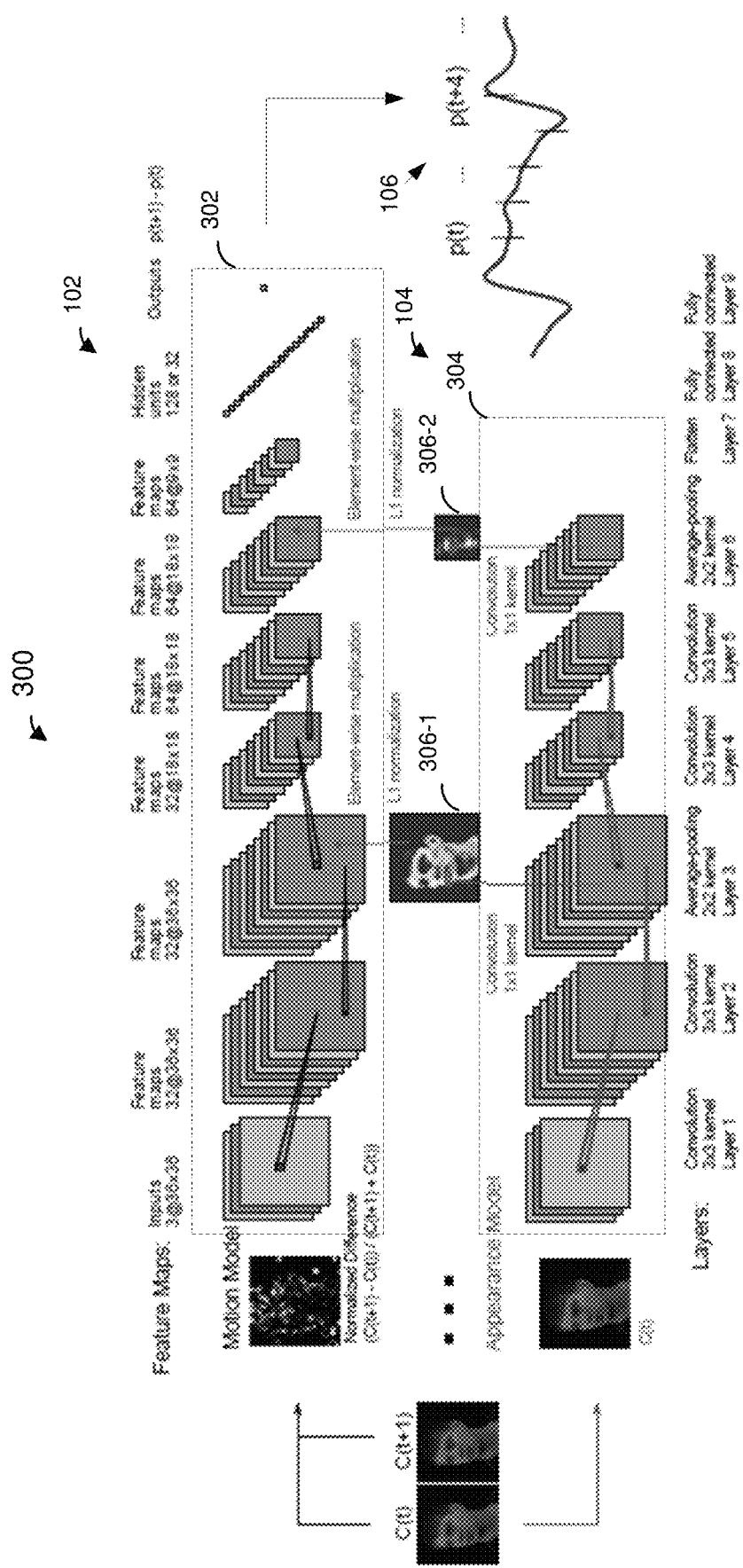
FIG. 3 is a block diagram illustrating an example implementation of the video-based physiological measurement system of FIG. 1, according to an embodiment.

FIG. 3 is a block diagram illustrating an example implementation 300 of the video-based physiological measurement system 100, according to an embodiment. In the embodiment of FIG. 3, the physiological signal measurement module 102 comprises a convolutional neural network 302. The neural network 302 may receive, as an input, the motion representation 114 generated based on frames of the video frame sequence 108, and may determine the physiological signal 106 based on the motion representation 114. The neural network 302 may additionally receive appearance representations (e.g., attention masks) generated based on the frames of the video frame sequence 108, and may utilize the appearance representations to focus on regions, within the frames of the video frame sequence 108, that exhibit stronger measures of the physiological signal 106. The neural network 302 may utilize a visual geometry group (VGG) neural network architecture, or may utilize another suitable neural network architecture. The neural network 302 comprises nine layers, of which layers 1, 2, 4 and 5 are convolutional layers, layers 3 and 6 are pooling layers, layer 7 is a flattening layer and layers 8 and 9 are fully connected layers, in the illustrated embodiment. In other embodiments, the neural network 302 comprises other suitable numbers of layers and/or layers arranged on other suitable configurations.

With continued reference to FIG. 3, each of the convolutional layers 1, 2, 4 and 5 may utilize a 3×3 kernel. In other embodiments, other suitable kernel sizes may be utilized. The pooling layers 3 and 6 may down-sample outputs of, respectively, convolutional layers 2 and 5 to reduce dimensionality of, respectively, output of the convolutional layers 2 and 5. For example the pooling layer 3 reduces output dimensions of the convolution layer 2 from 36×36 to 18×18, in the illustrated embodiment. Similarly, the pooling layer 6 reduces output dimensions of the convolution layer 5 from 18×18 to 9×9, in the illustrated embodiment. In an embodiment, the pooling layers pooling layers 3 and 6 use average pooling to reduce dimensionality by combining more important features with less important features in the preceding convolutional layer. Combining more important features with less important features, rather than discarding the less important features, average pooling, as compared to maximum (max) pooling, may lead to more accurate recovery of the physiological signal 106. For example, a physiological signal with a higher signal-to-noise ratio may be recovered as compared, for example, to a system in which max pooling is utilized to keep only the more important features from the previous layer. In another embodiment, however, pooling layers of the neural network 302 may utilize other pooling techniques, including max pooling techniques.

In an embodiment, the neural network 302 may utilize a symmetric activation function as the activation function of the hidden layers of the neural network 302. For example, in an embodiment, a hyperbolic tangent (tan h) function is utilized as the hidden layer activation functions in the neural network 302. Symmetry of the tan h functions may lead to better performance of the neural network 302 as compared to systems in which other activation functions, such as rectified linear units (ReLU), are utilized. In other embodiments, however, suitable activation functions other than tan h, including the ReLU, may be utilized. The last layer (e.g., layer 9 in the illustrated embodiment) of the neural network 302 may comprise one or more linear activation units and an error function, which may be, for example, a mean square error (MSE) function.

Referring still to FIG. 3, the appearance module 104 may comprise a neural network 304. The neural network 304 may generally be the same as the neural network 302, and may comprise some layers corresponding to the layers of the neural network 302. For example, the neural network 304 may comprise convolutional and pooling layers corresponding to convolutional and pooling layers 1-6 of the neural network 302, and may omit the last three layers (layers 7-9) of the neural network 302, in an embodiment. The neural network 304 may receive, as an input, respective raw video frames in the video frame sequence 108. In an embodiment, prior to being provided to the neural network 302, each raw frame in the video frame sequence 108 may be centered to zero mean and/or may be scaled to unit standard deviation. The neural network 304 may determine or synthesize a respective soft attention mask by applying a 1×1 filter to an output of a respective convolutional layer immediately preceding each pooling layer of the neural network 304. For example, the neural network 304 may determine or synthesize a first soft attention mask 306-1 at the output of the convolutional layer 2 of the neural network 304, for example by applying a 1×1 filter to the output of the convolutional layer 2 of the neural network 304. The neural network 304 may also determine or synthesize a second soft attention mask 306-2 at the output of the convolutional layer 5 of the neural network 304, for example by applying a 1×1 filter to the output of the convolutional layer 5 of the neural network 304. Because the soft attention mask 306-1 and the soft attention mask 306-2 are obtained at different-dimension levels of the neural network 304, the soft attention mask 306-1 and the soft attention mask 306-2 are synthesized from different levels of appearance features.

In an embodiment, the neural network 304 may calculate the soft attention mask at an output of a convolutional layer j that immediately precedes a pooling layer according to $$q^j = \frac{H_j W_j \cdot \sigma(w^{jT} x_a^j + b^j)}{2\|\sigma(w^{jT} x_a^j + b^j)\|_1} \quad \text{Equation 11}$$

where $x_a^j \in \mathbb{R}^{C_j \times H_j \times W_j}$ is the feature map at the output of the convolutional layer j, $C_j$, $H_j$, and $W_j$ are, respectively, color channel, height and width dimensions of the convolutional layer j, $w_j \in \mathbb{R}^{C_j}$ is a 1×1 convolutional kernel, $b^j$ is a bias, and $\sigma(\cdot)$ is a Sigmoid function. The Sigmund function may be followed by L1 normalization. Using a Sigmoid function as the activation function for obtaining an attention mask, and following the Sigmoid function by L1 normalization, may lead to a softer, less extreme, attention mask, as compared to a system that may utilize a softmax activation function. In some embodiments, however, the attention mask may be obtained in other suitable manners, including using a softmax as the activation function.

An attention mask obtained from a feature map at an output of a layer j of the neural network 304 is applied to a feature map at the output of the corresponding layer j of the neural network 302, in an embodiment. Thus, for example, the attention mask 306-1 synthesized from the feature map at the output of the convolutional layer 2 of the neural network 304 is applied to the feature map at the output of the convolutional layer 2 of the neural network 302, and the attention mask 306-2 obtained from the feature map at the output of the convolutional layer 5 of the attention neural network 304 is applied to the feature map at the output of the convolutional layer 5 of the motion neural network 302, in the illustrated embodiment.

In an embodiment, an attention mask obtained from a feature map at an output of a layer j of the neural network 304 is applied to a feature map at the output of the corresponding layer j of the neural network 302. For example, element-wise multiplication between the attention mask and the feature map is performed. In an embodiment, a masked feature map $z_m^j$ at the output of the layer j of the motion neural network 302 is obtained according to $$z_m^j = (\mathbb{1} \cdot q^j) \odot x_m^j \quad \text{Equation 12}$$

where $x_m^j \in \mathbb{R}^{C_j \times H_j \times W_j}$ is the feature map at the output convolutional layer j, $C_j$, $H_j$, and $W_j$ are, respectively, color channel, height, and width dimensions of the convolutional layer j, $\mathbb{1} \in \mathbb{R}^{C_j}$ is a vector of all ones, and $\odot$ signifies element-wise multiplication. The masked feature map $z_m^j$ may then be provided to a subsequent convolutional layer in the neural network 302. In an embodiment, the masked feature map may be provided to a pooling layer, and dimensionality of the masked feature map $z_m^j$ may be reduced prior to the feature map being provided to the subsequent convolutional layer.

Figure 4:
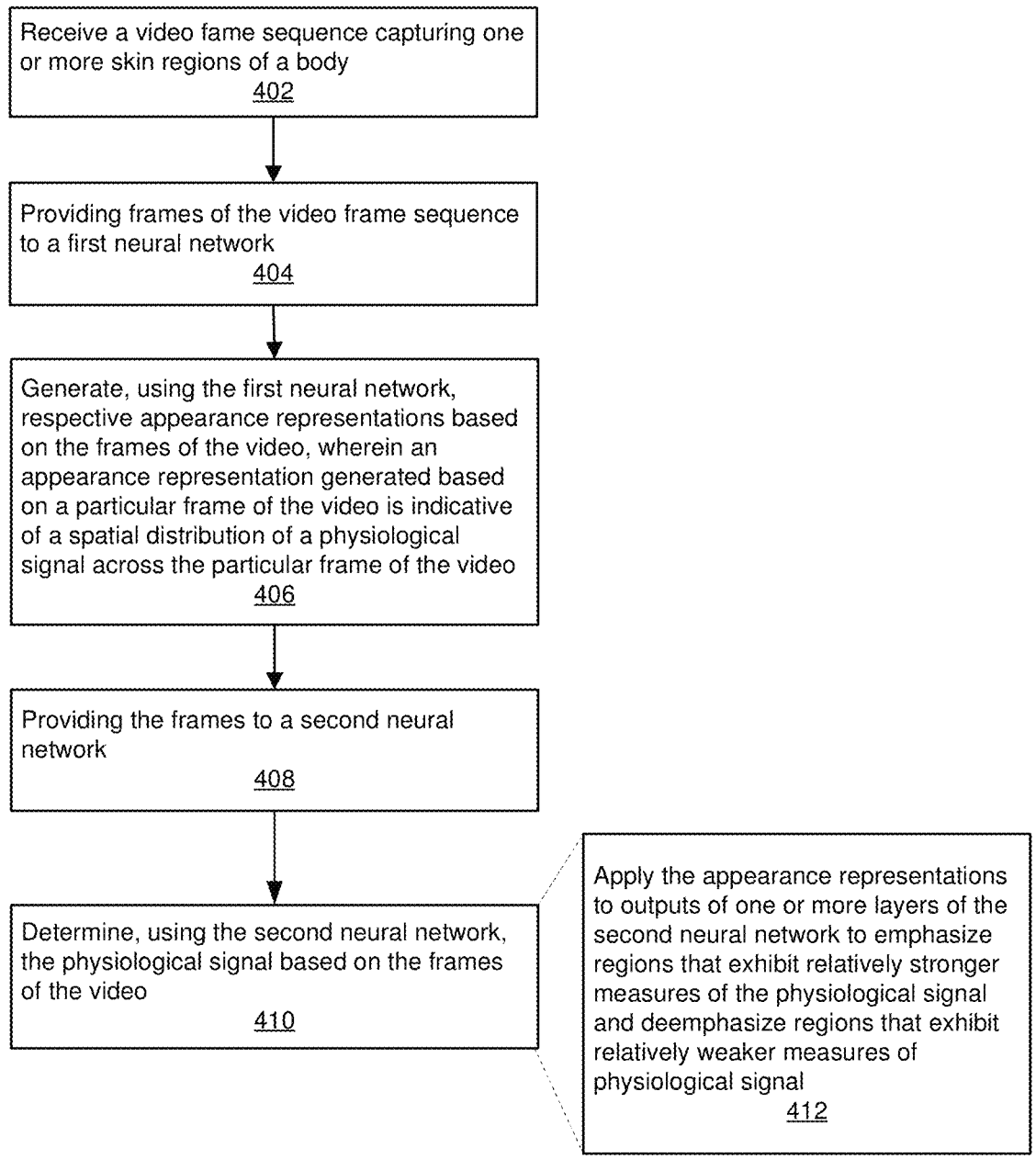
FIG. 4 is a flow diagram of a method for determining physiological signals, that may be implemented by the video-based physiological measurement system of FIG. 1, according to an embodiment.

FIG. 4 is a flow diagram of a method 400 for determining physiological signals based on frames of a video, according to an embodiment. In an embodiment, the method 400 is implemented in conjunction with the video-based physiological measurement system 100 of FIG. 1. In other embodiments, the method 500 is implemented in conjunction with video-based physiological measurement systems different from the video-based physiological measurement system 100 of FIG. 1

At block 402, a video frame sequence is received. The video frame sequence may capture one or more skin regions of a body. In an embodiment, the video frame sequence 108 of FIG. 1 is received. In another embodiment, a suitable video frame sequence different from the video frame sequence 108 of FIG. 1 is received. The video frame sequence may be of a human face, and may capture one or more skin regions in the human face. In other embodiments, the video frame sequence may capture skin regions in other suitable parts of the body. The video frame sequence may be obtained by a remote camera, and may be transmitted, via a suitable network, from the remote camera. As just an example, the video frame sequence may be obtained by a laptop or a smart phone camera and may be transmitted over any suitable wireless or wired network coupled to the laptop or the smart phone camera.

At block 404, frames of the video frame sequence received at block 402 are provided to a first neural network. For example, frames of the video frame sequence may be provided to a neural network of the appearance module 104. As a more specific example, frames of the video frame sequence may be provided to the neural network 304 of FIG. 3. In other embodiments, the video frame sequence are provided to suitable neural networks different from the neural network 304 of FIG. 3.

At block 406, respective appearance representations are generated based on the frames of the video frame sequence provided to the first neural network at block 404. An appearance representation generated based on a particular frame of the video frame sequence may be indicative of a spatial distribution of a physiological signal across the particular frame of the video frame sequence, In an embodiment, generating a particular appearance representation based on a particular frame comprises generating one or more attention masks based on the particular frame. For example, attention masks 306 of FIG. 3 may be generated. In other embodiments, other suitable appearance representations are generated.

At block 408, frames of the video frame sequence received at block 402 are provided to a second neural network. For example, frames of the video frame sequence may be provided to a neural network of the physiological signal measurement module 102. As a more specific example, frames of the video frame sequence may be provided to the neural network 302 of FIG. 3. In other embodiments, the video frame sequence are provided to suitable neural networks different from the neural network 302 of FIG. 3. In an embodiment, frames of the video frame sequence are provided to the second neural network at block 408 simultaneously with the frames of the video frame sequence being provided to the first neural network at block 404.

At block 410, the physiological signal is determined, using the second neural network, based on the frames of the video. For example, a blood volume pulse or a respiratory signal is determined, using the second neural network, based on the frames of the video. In other embodiments, other suitable physiological signals are determined, using the second neural network, based on the frames of the video. Block 410 may include block 412 at which the appearance representations generated by the first neural network at block 406 are applied to one or more layers of the second neural network, to emphasize regions that exhibit relatively stronger measures of the physiological signal and deemphasize regions that exhibit relatively weaker measures of physiological signal.

In some embodiment, the respective appearance representations generated at block 406 may additionally be provided as a separate output of the video-based physiological measurement system. For example, the appearance representations may be used to provide (e.g., display) the detected spatial-temporal distribution of the physiological signal in the video frame sequence received at block 402. The spatial-temporal distribution of the physiological signal may serve as an additional tool in conjunction with the physiological signal and/or physiological parameters obtained based on the physiological signal 106 to assess health of the subject, for example.

Figure 5:
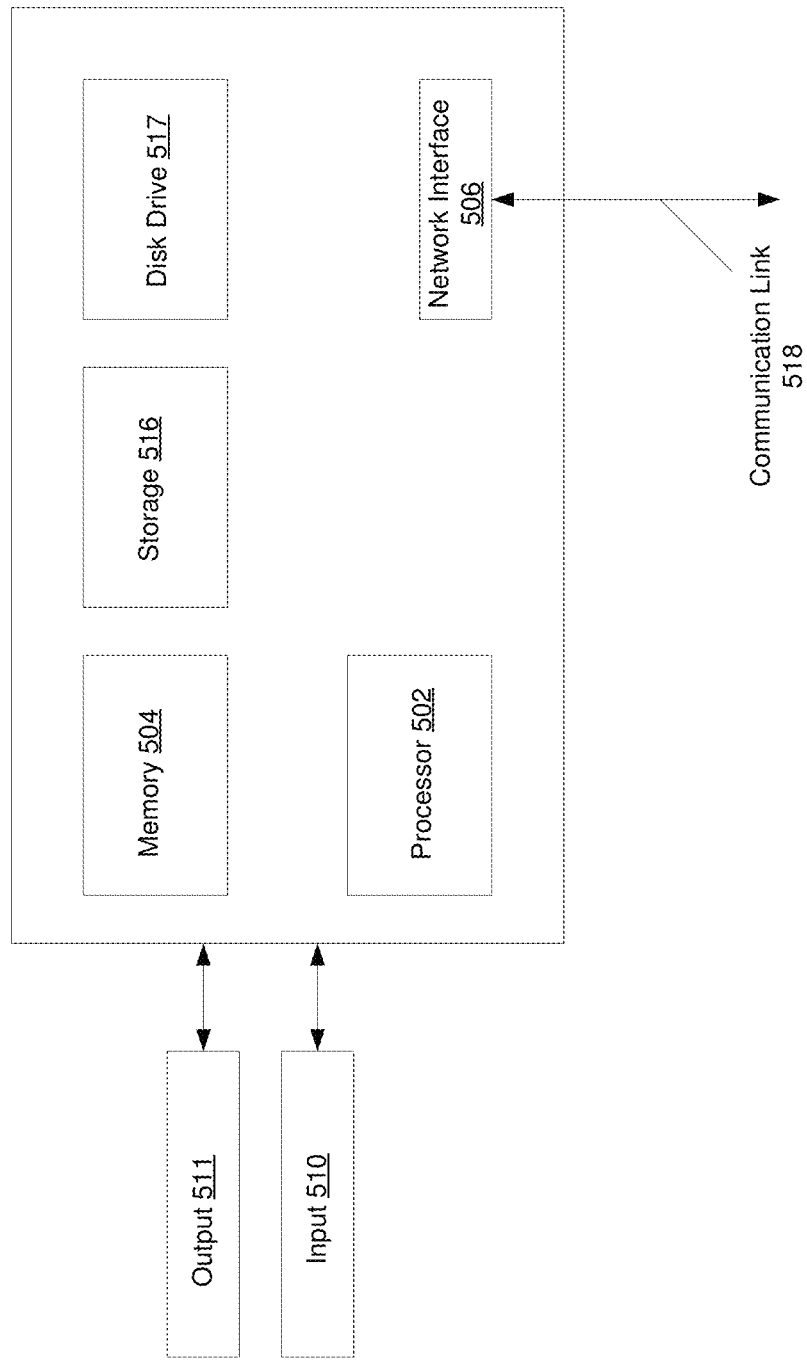
FIG. 5 is a block diagram of a computer system suitable for implementing one or more components of the video-based physiological measurement system of FIG. 1, according to an embodiment.

FIG. 5 is a block diagram of a computer system 500 suitable for implementing one or more embodiments of the present disclosure. In its most basic configuration, the computing system 500 may include at least one processor 502 and at least one memory 504. The computer system 500 may also include a bus (not shown) or other communication mechanism for communicating information data, signals, and information between various components of computer system 500. Components may include an input component 510 that processes a user action, such as selecting keys from a keypad/keyboard, selecting one or more buttons or links, etc., and sends a corresponding signal to the at least one processor 502. Components may also include an output component, such as a display, 511 that may display, for example, results of operations performed by the at least one processor 502. A transceiver or network interface 506 may transmit and receive signals between computer system 500 and other devices, such as user devices that may utilize results of processes implemented by the computer system 500. In one embodiment, the transmission is wireless, although other transmission mediums and methods may also be suitable.

The at least one processor 502, which can be a microcontroller, digital signal processor (DSP), or other processing component, processes these various signals, such as for display on computer system 500 or transmission to other devices via a communication link 518. The at least one processor 502 may also control transmission of information, such as cookies or IP addresses, to other devices. The at least one processor 502 may execute computer readable instructions stored in the memory 504. The computer readable instructions, when executed by the at least one processor 502, may cause the at least one processor 502 to implement processes associated with image generation and/or training.

Components of computing system 500 may also include at least one static storage component 516 (e.g., ROM) and/or at least one disk drive 517. Computer system 500 may perform specific operations by processor 512 and other components by executing one or more sequences of instructions contained in system memory component 504. Logic may be encoded in a computer readable medium, which may refer to any medium that participates in providing instructions to the at least one processor 502 for execution. Such a medium may take many forms, including but not limited to, non-transitory media, non-volatile media, volatile media, and transmission media. In various implementations, non-volatile media includes optical or magnetic disks, volatile media includes dynamic memory, such as system memory component 504, and transmission media includes coaxial cables, copper wire, and fiber optics. In one embodiment, the logic is encoded in non-transitory computer readable medium. In one example, transmission media may take the form of acoustic or light waves, such as those generated during radio wave, optical, and infrared data communications.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EEPROM, FLASH-EEPROM, any other memory chip or cartridge, or any other medium from which a computer is adapted to read.

In various embodiments of the present disclosure, execution of instruction sequences to practice the present disclosure may be performed by computer system 500. In various other embodiments of the present disclosure, a plurality of computer systems 500 coupled by communication link 518 to the network (e.g., such as a LAN, WLAN, PTSN, and/or various other wired or wireless networks, including telecommunications, mobile, and cellular phone networks) may perform instruction sequences to practice the present disclosure in coordination with one another.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

While various operations of an image synthesis system have been described herein in terms of "modules" or "components," it is noted that that terms are not limited to single units or functions. Moreover, functionality attributed to some of the modules or components described herein may be combined and attributed to fewer modules or components. Further still, while the present invention has been described with reference to specific examples, those examples are intended to be illustrative only, and are not intended to limit the invention. It will be apparent to those of ordinary skill in the art that changes, additions or deletions may be made to the disclosed embodiments without departing from the spirit and scope of the invention. For example, one or more portions of methods described above may be performed in a different order (or concurrently) and still achieve desirable results.

What is claimed is:

1. A computer-implemented method for measuring physiological parameters, the method comprising:
    receiving a video fame sequence capturing one or more skin regions of a body;
    providing frames of the video frame sequence to a first neural network;
    generating, using the first neural network, respective appearance representations based on the frames of the video frame sequence, wherein an appearance representation generated based on a particular frame of the video frame sequence is indicative of a spatial distribution of a physiological signal across the particular frame of the video frame sequence;
    simultaneously with providing the frames of the video frame sequence frame sequence to the first neural network, providing the frames to a second neural network; and
    determining, using the second neural network, the physiological signal based on the frames of the video frame sequence, including applying the appearance representations, generated by the first neural network, to outputs of one or more layers of the second neural network to emphasize regions, in the frames, that exhibit relatively stronger presence of the physiological signal and deemphasize regions, in the frames, that exhibit relatively weaker presence of physiological signal.

2. The method of claim 1, further comprising determining at least one physiological parameter based on the physiological signal.

3. The method of claim 1, wherein
    the first neural network comprises a convolutional attention network (CAN), and
    the second neural network comprises a convolutional neural network (CNN).

4. The method of claim 1, wherein
    generating the appearance representation comprises generating one or more attention masks based on respective feature maps generated at respective one or more layers of the first neural network, and
    applying the appearance representations comprises multiplying the one or more attention masks with feature maps generated by corresponding one or more layers of the second neural network.

5. The method of claim 4, wherein generating an attention mask, of the one or more attention masks, based on a feature map, of the respective feature maps, includes (i) computing weights corresponding to respective features in the feature map using a sigmoid activation function and (ii) computing L1-norms of the weights.

6. The method of claim 1, further comprising generating a motion representation based on a difference between two or more consecutive frames of the video frame sequence, wherein providing the frames to the second neural network comprises providing the motion representation to the second neural network, and wherein determining the physiological signal comprises determining the physiological signal based on the motion representation.

7. The method of claim 6, wherein generating the motion representation includes down-sampling pixels in the frames of the video frame sequence using bicubic interpolation to spatially average across pixels in the frames of the video frame sequence.

8. The method of claim 6, wherein generating the motion representation includes calculating first derivatives of time varying light reflection representations corresponding to respective pixels in the frames of the video frame sequence.

9. The method of claim 2, wherein the CNN comprises one or more average pooling layers that reduce dimensions of a preceding layers by averaging across features of the preceding layer.

10. The method of claim 2, wherein the CNN comprises one or more hyperbolic tangent (tan h) activation functions.

11. The method of claim 1, further comprising simultaneously training the first neural network and the second neural network using supervised training.

12. A system for measuring physiological parameters, the system comprising
    a data storage device that stores instructions for measuring physiological parameters based on frames of a video, and
    a processor configured to execute the instructions to perform a method including:
        receiving a video fame sequence capturing one or more skin regions of a body,
        providing frames of the video frame sequence to a first neural network,
        generating, using the first neural network, respective appearance representations based on the frames of the video frame sequence, wherein an appearance representation generated based on a particular frame of the video frame sequence is indicative of a spatial distribution of a physiological signal across the particular frame of the video frame sequence, simultaneously with providing the frames of the video frame sequence to the first neural network, providing the frames to a second neural network, and determining, using the second neural network, the physiological signal based on the frames of the video frame sequence, including applying the appearance representations, generated by the first neural network, to outputs of one or more layers of the second neural network to emphasize regions, in the frames, that exhibit relatively stronger presence of the physiological signal and deemphasize regions, in the frames, that exhibit relatively weaker presence of physiological signal.

13. The system of claim 12, wherein the processor is further configured to execute the instructions to perform the method including determining at least one physiological parameter based on the physiological signal.

14. The system of claim 12, wherein generating the appearance representation comprises generating one or more attention masks based on respective feature maps generated at respective one or more layers of the first neural network, and applying the appearance representations comprises multiplying the one or more attention masks with feature maps generated by corresponding one or more layers of the second neural network.

15. The system of claim 14, wherein generating an attention mask, of the one or more attention masks, based on a feature map, of the respective feature maps, includes (i) computing weights corresponding to respective features in the feature map using a sigmoid activation function and (ii) computing L1-norms of the weights.

16. The system of claim 15, the processor is further configured to execute the instructions to perform the method including generating a motion representation based on a difference between two or more consecutive frames of the video frame sequence, wherein providing the frames to the second neural network comprises providing the motion representation to the second neural network, and wherein determining the physiological signal comprises determining the physiological signal based on the motion representation.

17. The system of claim 12, wherein the second neural network is a convolutional neural network (CNN), and wherein the CNN comprise (i) one or more average pooling layers that reduce dimensions of a preceding layers by averaging across features of the preceding layer and (ii) one or more hyperbolic tangent (tan h) activation functions.

18. A tangible, non-transitory computer readable medium, or media, storing machine readable instructions that, when executed by one or more processors, cause the one or more processors to:

receive a video fame sequence capturing one or more skin regions of a body, provide frames of the video frame sequence to a first neural network, generate, using the first neural network, respective appearance representations based on the frames of the video frame sequence, wherein an appearance representation generated based on a particular frame of the video frame sequence is indicative of a spatial distribution of a physiological signal across the particular frame of the video frame sequence, simultaneously with providing the frames of the video frame sequence to the first neural network, provide the frames to a second neural network, and determine, using the second neural network, the physiological signal based on the frames of the video frame sequence, including applying the appearance representations, generated by the first neural network, to outputs of one or more layers of the second neural network to emphasize regions, in the frames, that exhibit relatively stronger presence of the physiological signal and deemphasize regions, in the frames, that exhibit relatively weaker presence of physiological signal.

19. The tangible, non-transitory computer readable medium, or media, of claim 18, wherein:

generating the appearance representation comprises generating one or more attention masks based on respective feature maps generated at respective one or more layers of the first neural network, and applying the appearance representations comprises multiplying the one or more attention masks with feature maps generated by corresponding one or more layers of the second neural network.

20. The tangible, non-transitory computer readable medium, or media, of claim 18, further storing machine readable instructions that, when executed by one or more processors, cause the one or more processors to generate a motion representation based on a difference between two or more consecutive frames of the video frame sequence, wherein providing the frames to the second neural network comprises providing the motion representation to the second neural network, and wherein determining the physiological signal comprises determining the physiological signal based on the motion representation.

* * * * *